United States Patent [19]

Briggs et al.

[11] Patent Number: 4,979,515

[45] Date of Patent: * Dec. 25, 1990

[54] SYSTEM FOR OBTAINING BLOOD SAMPLES AND SUBMITTING FOR TESTING OF AIDS

[76] Inventors: David Briggs; Brenda Briggs; both of 4400 Trenton, Ste. G, Metaire, La. 70006; Kent Leger, 1221 Amelia St., New Orleans, La. 70115; David J. Bourgeois; James W. Briggs, both of 4400 Trenton, Ste. G, Metaire, La. 70006

[*] Notice: The portion of the term of this patent subsequent to Oct. 18, 2005 has been disclaimed.

[21] Appl. No.: 258,780

[22] Filed: Oct. 17, 1988

Related U.S. Application Data

[63] Continuation of Ser. No. 51,947, May 20, 1987, Pat. No. 4,777,964.

[51] Int. Cl.$^5$ .............................................. A61B 10/00
[52] U.S. Cl. ................................... 128/760; 206/569; 604/256
[58] Field of Search ............... 128/760, 763, 764, 769, 128/770; 206/569, 572; 422/61; 604/256

[56] References Cited

U.S. PATENT DOCUMENTS

| | | | |
|---|---|---|---|
| 2,437,408 | 3/1948 | Soet | 128/764 |
| 3,203,540 | 8/1965 | Kalt et al. | 206/569 |
| 3,272,319 | 9/1966 | Brewer | 206/569 |
| 4,122,947 | 10/1978 | Falla | 128/760 |
| 4,294,931 | 10/1981 | Levin et al. | 422/61 |
| 4,393,882 | 7/1983 | White | 128/763 |
| 4,576,595 | 3/1986 | Aas et al. | 128/763 |
| 4,617,278 | 10/1986 | Reed | 422/61 |
| 4,777,964 | 10/1988 | Briggs et al. | 128/760 |

Primary Examiner—Stephen C. Pellegrino
Attorney, Agent, or Firm—Pravel, Gambrell, Hewitt, Kimball & Krieger

[57] ABSTRACT

A blood sampling kit having a plurality of glass vials for receiving blood therein; a puncture pin for puncturing the skin of the subject to be tested; an alcohol swab for cleansing the area punctured, and an envelope for returning the specimen to a laboratory. The specimen receiving kit further comprises a quantity of clay like material for sealing the ends of the blood vials after the blood sample has been received therein, so that blood is not lost during transit. The system provides that the test subject would receive the kit containing the above-referenced items to prick one's finger, place blood into the plurality of blood-receiving vials, close off the end of the vials with a quantity of clay plug; return the vials to the kit, reseal the blood it, place the kit in a sealable plastic bag container, note one's name and address on the plastic bag and place the kit in an envelope provided for returning to the laboratory for testing. Of course, following testing, the subject is notified of the results of the test through the mail. Therefore, the test procedures can be undertaken through the mail without personal appearances at the laboratory.

9 Claims, 3 Drawing Sheets

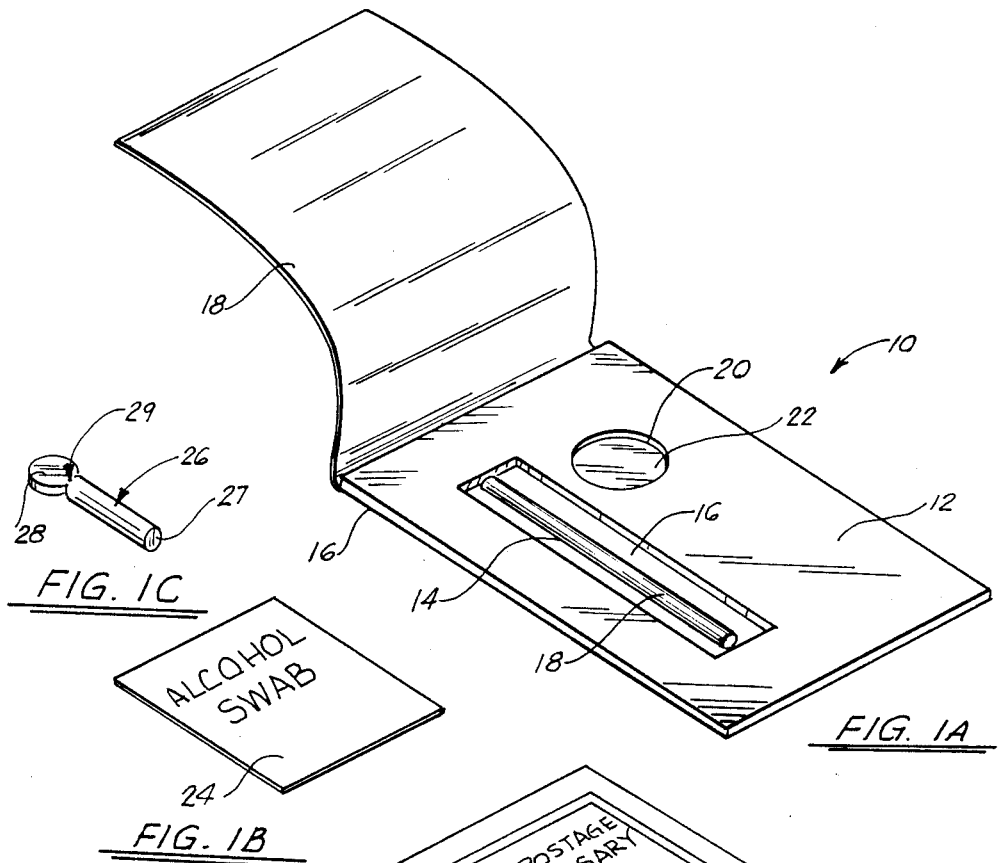
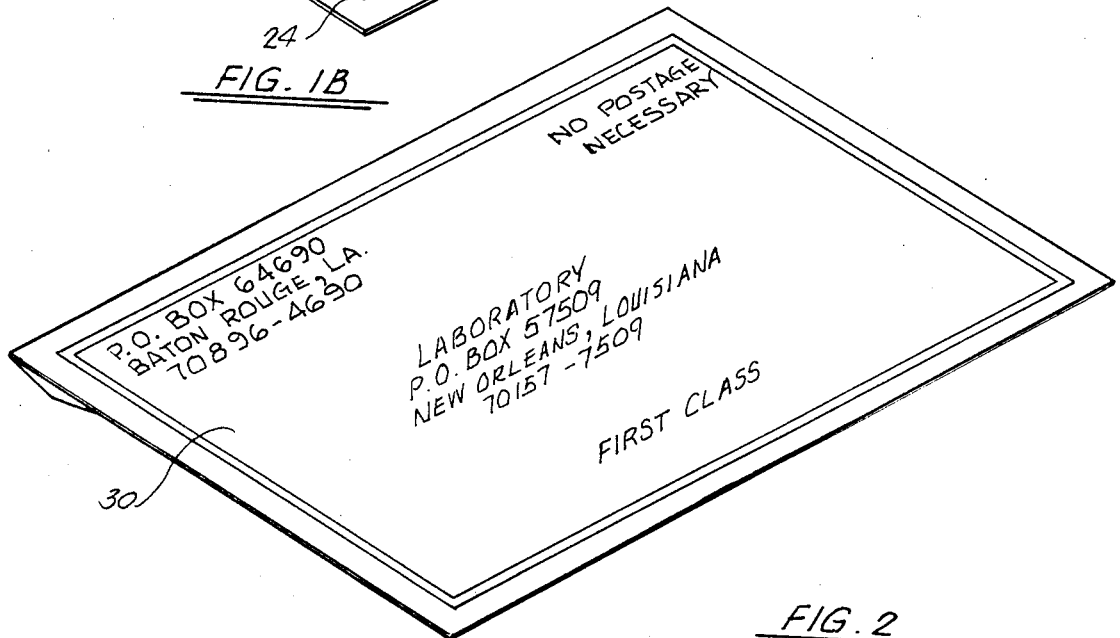

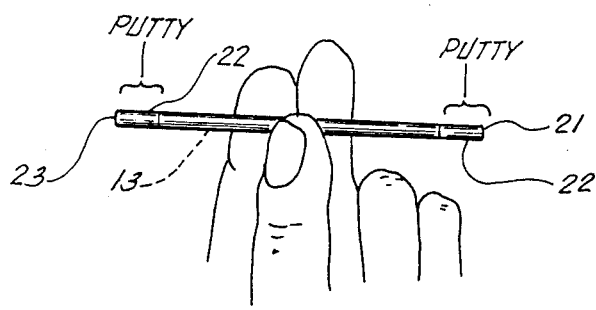
FIG. 4
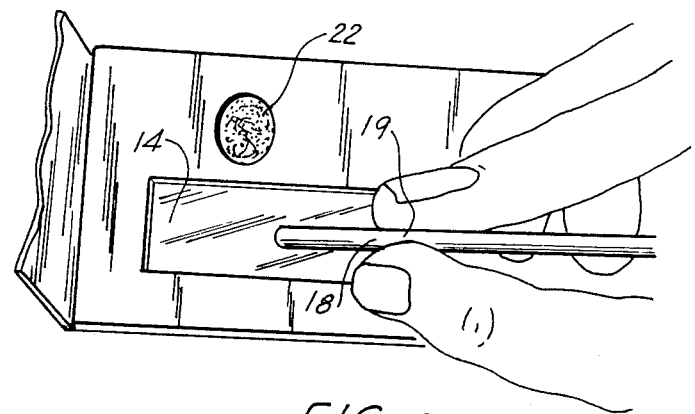
FIG. 5
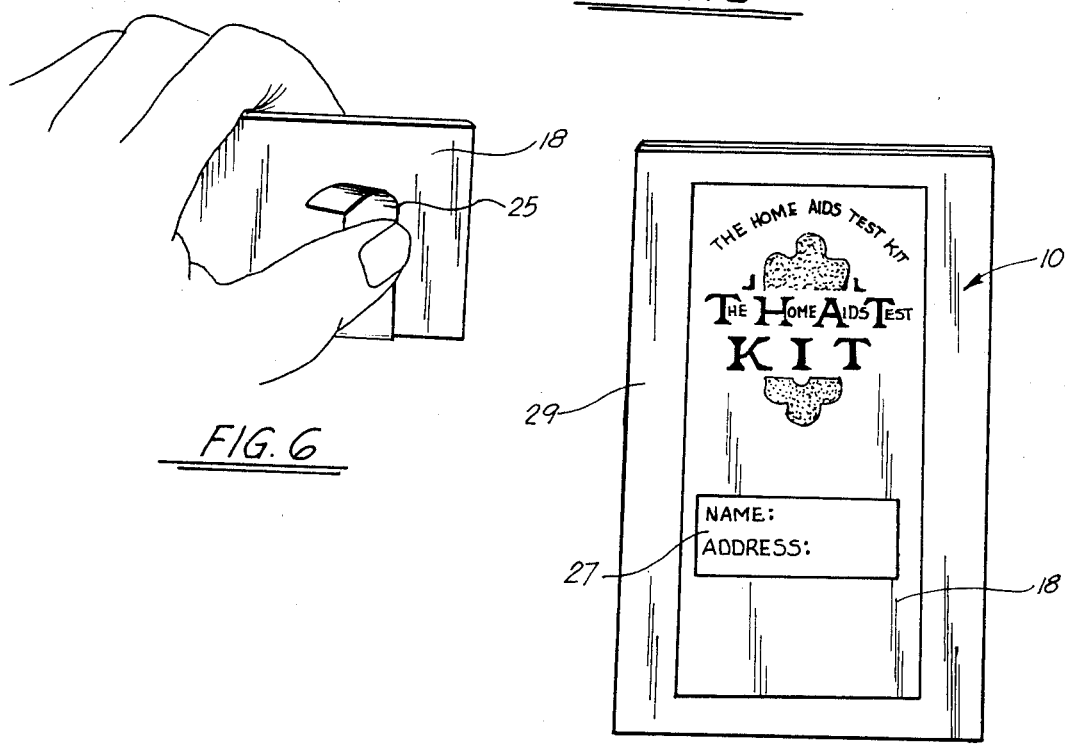
FIG. 6
FIG. 7

SYSTEM FOR OBTAINING BLOOD SAMPLES AND SUBMITTING FOR TESTING OF AIDS

This is a continuation of application Ser. No. 051,947 filed on May 20, 1987, which issued as U.S. Pat. No. 4,777,964 on Oct. 18, 1988 by the same inventors.

BACKGROUND OF THE INVENTION

1. Field of the Invention

The present invention relates to testing for foreign agents in blood. More particularly, the system of the present invention relates to an individual obtaining a blood sample and submitting the sample to a testing laboratory for testing for any bacterial, viral or chemical agent, including the AIDS virus in the blood.

2. General Background

One of the most serious health concerns of the present day is the presence of the AIDS virus in the national population. The AIDS virus is by all accounts a virus that, when a person becomes infected with it, eventually meets death. The disease, although at this time, being more prevalent in the gay community, has become a general concern of the national population, and for the medical community, poses a serious threat to the contamination of the national blood supply.

It is essential, therefore, that there be a system whereby individuals who are concerned as to whether or not they may have contracted AIDS, or their blood system carries the AIDS virus, to be provided with a convenient test for detecting same. There is an ever-pressing need for any individuals who may have had personal contact with a high risk group, that they can be informed, through a convenient testing system, whether or not they have contacted the AIDS virus. Of course, even for those who wish to donate blood, or to satisfy their own personal concerns, may wish to submit to a convenient test which would ease their concern as to whether or not they have contracted AIDS. Although the discussion of the test would concern itself primarily with the AIDS virus, it should be made clear that the self-testing by the individual can be conducted in order to ascertain whether or not there are other foreign agents in the blood such as any bacterial, viral or chemical agents. The process and apparatus of the present invention could be utilized for a broad range of such tests, and is not solely limited to ascertaining whether one's blood contains the AIDS virus.

There appears, at this time, to be no simple and reliable system whereby an individual can undergo such a test, without having to submit oneself to hospitalization or testing at a clinic. Test kits of various types which have been developed for personal use, which are readily available are well known. What follows are patents formed which contain pertinent art in this field:

| Pat. No. | Title of Patent | Inventor |
|---|---|---|
| 4,520,113 | "Seroloagical Detection Of Antibodies To HTLV -III I Sera Of Patients With AIDS And Pre-AIDS Conditions" | Gallo, et al |
| 4,382,062 | "Test Agent For The Detection Of Coupling Compounds, And A Process For Its Preparation" | Kohl |
| 4,365,970 | "Specimen Test Slide And Method For Testing Occult Blood" | Lawrence, et al |

-continued

| Pat. No. | Title of Patent | Inventor |
|---|---|---|
| 4,329,317 | "Method Of Stabilizing A Specimen Slide For Occult Blood Testing" | Detweiler, et al |
| 4,240,547 | "Specimen Mailer" | Taylor |
| 4,122,947 | "Pre-Packaged Patient Identification Kit" | Falla |
| 3,917,456 | "Alcohol Breath Testing Kit" | Eckstein, et al |
| 3,272,319 | "Immunological Test Kit" | Brewer |
| 3,203,540 | "Test Kit" | Kalt, et al. |

SUMMARY OF THE PRESENT INVENTION

The present invention provides a system for whomever wishes to ascertain whether or not he is carrying the AIDS virus, to perform a blood sampling and to forward the sample to a lab for further testing. This test kit and its collection methodology can collect and be used to submit blood samples for any of many bacterial, viral or chemical components. What is provided is a blood sampling kit having a plurality of glass vials for receiving blood therein; a puncture pin for puncturing the skin of the subject to be tested; an alcohol swab for cleansing the area punctured, and an envelope for returning the specimen to a laboratory. The specimen receiving kit further comprises a quantity of clay like material for sealing the ends of the blood vials after the blood sample has been received therein, so that blood is not lost during transit. The system provides that the test subject would receive the kit containing the above-referenced items to prick one's finger, place blood into the plurality of blood-receiving vials, close off the end of the vials with a quantity of clay plug; return the vials to the kit, reseal the blood it, place the kit in a sealable plastic bag container, note one's name and address on the plastic bag and place the kit in an envelope provided for returning to the laboratory for testing. Of course, following testing, the subject is notified of the results of the test through the mail. Therefore, the test procedures can be undertaken through the mail without personal appearances at the lab.

Therefore, it is an object of the present invention to provide a method for a test subject to obtain blood and to have the blood tested for the AIDS virus;

It is a further object of the present invention to provide a test system whereby the subject can return vials of blood sealed in containers taken from himself, have the blood undergo a lab analysis, and the results returned to him all without his leaving the confines of his home;

It is still a further object of the present invention to provide a blood sampling system for AIDS whereby the system enables the subject to have a quantity of blood to be tested, the quantity of blood forwarded by the subject in a sealed package for receiving the results after testing; and It is still a further principal object of the present invention to provide a system whereby an individual may obtain blood samples in privacy, submit the samples to a lab for analysis, so that the analysis may include analysis for any bacterial, viral or chemical components in the blood.

These and other objects of this invention will be readily apparent to those skilled in the art from the detailed description and claims which follow.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIGS. 1A through 1C, illustrate the various components contained in the blood sampling kit for AIDS;

FIG. 2 is an overall perspective view of the envelope for returning the sample blood in the kit as seen in FIGS. 1A through 1C;

FIG. 4 is an illustration of a sealed blood vial containing the blood of the subject for testing;

FIG. 5 is a view of the sealed blood vial containing blood being returned into the kit for forwarding to the laboratory;

FIG. 6 is a partial view of the kit being sealed for returning to the laboratory for testing; and FIG. 7 is a front view of the kit that is placed in the envelope as illustrated in FIG. 2 and further illustrating the plastic bag container of the pocket for the test to be conducted.

DETAILED DESCRIPTION OF THE PREFERRED EMBODIMENT

Figure 3A:
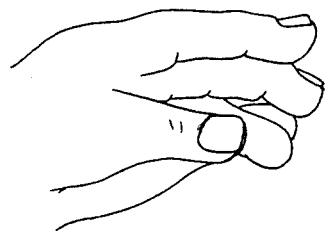
FIGS. 3A through 3D are the schematic steps illustrating the obtaining and placing of blood into blood-receiving vials of the kit.

The preferred embodiment of the system of the present invention is illustrated in FIGS. 1 through 7 as a series of components and steps involved in the system. The overall system involves an individual or layman subject obtaining a kit known in the market as the "The Home Aids Test Kit", and obtaining a sample of blood for forwarding to a laboratory for testing. FIGS. 1A through 1C illustrates the components of the kit itself, the kit being designated by the numeral 10. What is provided is a base member 12 which could be thickened rectangular portion of cardboard or the like material having a backing 16, and a front-flap cover 18 as seen in FIG. 1A. Base member 12 further comprises an elongated blood vial containing pocket 14 which actually comprises a section of the backing 12 cut out so that the backing 16 serves as the floor portion for the vial containing portion 14. As illustrated in FIG. 1A the vial containing portion 14 contains a sample blood vial 18 which, in the preferred embodiment is simply a glass tube having a hollow bore therethrough for blood being contained therein for testing. Base member 12 further comprises a circular cutaway section 20 housing a quantity of clay or puddy 22 or the like substance, the function of which shall be illustrated further. As purchased, the flat member 18 is normally in the down position as seen in FIG. 7 with a plurality of three (3) to four (4) blood vials 18 contained in blood vial containing portion 14 and the quantity of clay 22 contained in the clay containing portion 20. There is further provided in the kit an alcohol swab 24 which is simply a quantity of cotton or the like soaked in alcohol for cleaning any portion of the skin that must be utilized in the testing. Further, there is provided a finger-pricking element 26 which includes a body portion 27 and cap 28 with a needle 29 as seen in phantom view stuck into the cap portion 28 so that no inadvertent pricking will take place.

Figure 3B:
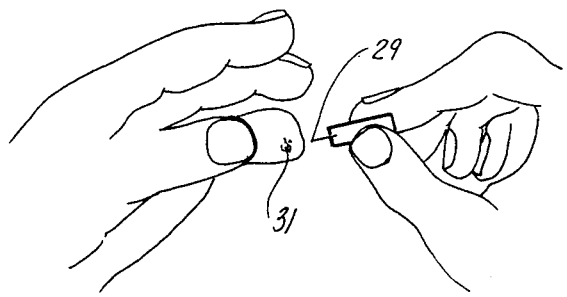
Figure 3C:
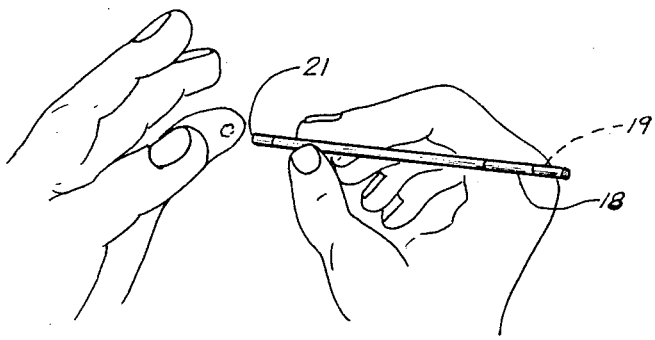
Figure 3D:
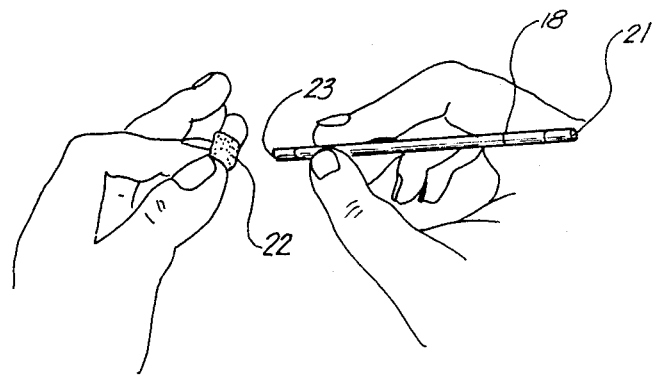

Turning now to the actual blood sampling that is to be performed, reference is made to FIGS. 3A through 3D, and FIG. 4 through FIG. 6. After one has received the kit, as illustrated in FIGS. 1A through 1C and 7, the flat member is placed on the open position which would reveal the blood vials and clay member 22. Alcohol swab 24 is then utilized to clean the portion of the skin, usually the first digit of the forth finger, which must be pricked to receive blood. Following the cleaning with alcohol swab 24, the cap portion 28 of the finger pricking member 26 is removed, and needle 29 is jabbed quickly into the skin to break the dermis layer and obtain a quantity or drop of blood 31 on the end of the finger, as seen in FIG. 3A and 3B. Following the pricking of the finger, a blood vial 18 is then placed upon the spot of blood 31 and blood runs into the internal bore 19 of blood vial 18 to substantially fill it with blood. Following the placing of blood into the blood vial 18, as seen in FIG. 3C, the end of the blood vial is then pushed into the quantity of clay 22 so that a portion of the clay remains in the bore 19 of blood vial 18 to seal its ends so that blood cannot be released therefrom. Following that procedure, the second end portion 23 of blood vial 18 is sealed in clay portion 22 so that both end portion s21 and 23 contain a portion of clay or puddy 18 therein as seen in FIG. 4. Therefore, the blood 13 contained in vial 18 is secured therein until the actual testing.

Blood is received into all three (3) or four (4) blood vials and each sealed with clay 22 at the end portions so that the laboratory is able to receive a reasonable quantity of blood. Utilizing each blood vial, the sealed vials 18 are then replaced back into blood vial chamber 14 as seen being done in FIG. 5. Following that step, the top flat member 18 is then secured in the down position and sealed with a quantity of sealing type 25 so that the blood vials containing the subject's blood are now ready for shipment to the laboratory. As seen in FIG. 7, the sealed kit is placed in plastic bag container 29; and the patient's name and address placed on identification label 27. The kit in the plastic bag 29 is then placed into envelope 30 as seen in FIG. 2, and envelope 30 is sealed and forwarded to the laboratory. Following the testing procedures by the laboratory, the test results are then returned to the sender through the mail, and the subject is then notified as to whether or not his blood does in fact contain the AIDS virus.

It is foreseen that in the use of test, that this test could be sold over the counter and could be done quite efficiently and easily at one's home. "The Home Aids Test Kit" is a unique system in which, due to personal misgivings about going to a hospital or clinic, a concerned subject may ascertain quite easily whether or not his blood does in fact contain the AIDS virus. This logic also extends to submissions of blood samples for the analysis of any and many other viral, bacterial or chemical testing.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A blood sampling kit utilized by a person for the person to collect his own blood specimen and submit the specimen for subsequent analysis by a laboratory, the kit comprising:

(a) a means for a person to rupture ones dermis layer of skin so that ones blood is released therefrom;

(b) at least one blood receiving member, further comprising a collection tube having first and second open end portions and a bore therethrough for receiving ones blood specimen thereinto;

(c) means contained in the shipping container for plugging the end portions of the bore of the collection tube containing ones blood specimen;

(d) shipping container, further comprising a body portion having a first and section for receiving the sealed collection tube containing ones blood specimen thereinto; and (e) means sealable over the face of the shipping container for sealing the container containing ones blood specimen within the seal container so that the seal container may be shipped by the person to a laboratory for analysis.

2. The blood sampling kit in claim 1, wherein the collection tube comprises a capillary tube.

3. The blood sampling kit in claim 1, further comprising an alcohol containing member for disinfecting ones portion of the skin that is ruptured during the test.

4. The blood sampling kit in claim 1, included a plurality of collection tubes for receiving ones blood therein for submitting to the testing laboratory for analysis.

5. The blood sampling kit in claim 1, wherein there is further included an identification tag for allowing the person submitting the specimen to include ones name and address for proper identification.

6. A method for having a person collect his own blood specimen and submit the specimen for subsequent analysis for bacterial, viral or chemical components in the blood specimen, the method comprising the following steps:

(a) providing a blood collection kit, the kit including at least means for pricking ones skin for drawing blood, a capillary tube having first and second open end portions and a bore therethrough for receiving blood drawn therefrom, and means contained in the collection kit to seal the capillary tube containing ones blood;

(b) pricking ones finger to draw blood;

(c) introducing a quantity of ones blood into the bore of the capillary tube through capillary action in an amount sufficient to conduct blood tests on the quantity of blood;

(d) sealing the open ends of the capillary tube containing the quantity of blood into the formable material so that the blood is sealed within the bore of the capillary tube;

(e) placing the sealed capillary tube containing ones blood into the blood collection kit; and (f) sealing the blood collection kit and forwarding the blood collection kit containing the blood specimen to a laboratory for analysis.

7. The method in claim 6, wherein the kit further provides a container for placing the blood containing collection tubes therein for forwarding to the laboratory.

8. The method in claim 6, wherein the container housing ones sealed collection tubes of blood is identified through ones name and address identification tag.

9. The method in claim 6, wherein the container houses a plurality of capillary tubes for collecting multiple samples of blood.

* * * * *